US006589518B2

(12) United States Patent
Steer

(10) Patent No.: US 6,589,518 B2
(45) Date of Patent: *Jul. 8, 2003

(54) MOUSSE FORMING HAIR TREATMENT COMPOSITION

(75) Inventor: David Charles Steer, Merseyside (GB)

(73) Assignee: Unilever Home & Personal Care USA, division of Conopco, Inc., Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/151,525

(22) Filed: May 20, 2002

(65) Prior Publication Data

US 2002/0192166 A1 Dec. 19, 2002

Related U.S. Application Data

(63) Continuation-in-part of application No. 09/559,213, filed on Apr. 26, 2000, now Pat. No. 6,395,258.

(30) Foreign Application Priority Data

Apr. 27, 1999 (GB) .............................................. 9909711

(51) Int. Cl.$^7$ ........................ A61K 7/11; A61K 7/075; A61K 7/00
(52) U.S. Cl. ........................ 424/70.1; 424/45; 424/47; 424/70.12; 424/70.13; 424/70.17
(58) Field of Search ........................ 424/47, 45, 70.1, 424/70.12, 70.13, 70.17, 400, 401

(56) References Cited

U.S. PATENT DOCUMENTS 3,655,865 A    4/1972  Murphy

FOREIGN PATENT DOCUMENTS

| EP | 0818190 A2 | 1/1998 |
| EP | 0820755 A2 | 1/1998 |
| WO | 95/05158 | 2/1995 |
| WO | 96/32921 | 10/1996 |
| WO | 98/19654 | 5/1998 |

*Primary Examiner*—Shelley A. Dodson
(74) *Attorney, Agent, or Firm*—Milton L. Honig

(57) ABSTRACT

A mousse forming hair treatment composition, which may be a cleansing and/or conditioning composition, comprising a foamable concentrate comprising at least one surfactant, an aqueous carrier, and which is substantially free of anionic surfactants, and an aerosol propellant.

11 Claims, No Drawings

MOUSSE FORMING HAIR TREATMENT COMPOSITION

This is a continuation-in-part of Ser. No. 09/559,213, filed Apr. 26, 2000 now U.S. Pat. No. 6,395,258.

This invention relates to mousse forming hair treatment compositions. More particularly, the invention relates to mousse forming hair treatment compositions, which may preferably be shampoos, which have improved foaming ability in the hair, and which may also deliver styling and setting properties from the delivery of anionic styling polymers.

It is known to try to provide mild surfactant based cleansing compositions for use on the hair and/or skin. It is also well known that, of the various surfactant types, that anionic surfactants are generally speaking the most harsh category of surfactants, even though they are desirable from a consumer point of view, because of the relatively high degree of lathering that they produce, with the consequent desirable sensory attributes.

Further it is known to provide so-called "three in one" hair care compositions, which are capable of cleaning, conditioning and styling the hair. Other associated benefits of such compositions may include curl retention, bodifying, stiffness and setting properties, with all such properties being supposedly deliverable from a single composition. An example of such a teaching is to be found in WO97/38673 (Stepan Company). In this application, the various benefits described above are said to be delivered from the hair care composition comprising 1 to 80% of a nonionic, semi polar nonionic, or amphoteric surfactant, or mixtures thereof, from 0.1 to 10% of a second surfactant which is a cationic surfactant, a fatty amine salt or mixtures thereof, and 0.001 to 10% by weight of an anionic polymer.

However, a problem with cosmetic compositions which are generally free of anionic surfactants (that is, they are based for example on nonionic, amphoteric and/or cationic surfactants) is that they have a tendency not to foam adequately, or may have poor sensory properties associated with foaming, such as a tendency for any foam that does generate to generate slowly, to spread slowly or to dissipate quickly. In the same way that foaming of a cosmetic composition, such as for example of a shampoo composition, is recognised as being a desirable attribute in a cosmetic product, generally leading to favourable consumer perceptions, so a product which does not foam, or does not foam adequately or with a suitable foam quality generally has perceived consumer negatives.

WO98/08149, the content of which is incorporated herein by reference, is representative of the art which describes mousse hair compositions, but it is silent on compositions which do not contain anionic surfactants, and indeed contains no teaching of a surfactant composition which is specifically free of any anionic surfactant.

It is thus an object of the invention to provide a cosmetic composition which contains one or more surfactants, yet is substantially free of any anionic surfactants, and yet provides improved levels of foaming.

We have surprisingly found that in a hair treatment composition which is a shampooing composition, be it of the conventional or "2-in-1" type, that it is possible to improve the foaming capabilities and characteristics of an aqueous surfactant composition which is substantially free of anionic surfactants, by providing the surfactant composition in the form of a mousse forming concentrate, which can be combined with a propellant gas to provide a mousse forming composition. Thus, we have found that the foaming properties of an aqueous surfactant-containing composition which does not contain any substantial levels of anionic surfactant may be improved by the provision of such a composition in the form of a mousse.

Thus, according to a first aspect of the invention, there is provided a mousse forming hair treatment composition, which is preferably shampoo composition (optionally of the "2-in-1" type) and comprising a foamable concentrate comprising at least one surfactant, an aqueous carrier, and which is substantially free of anionic surfactants, and an aerosol propellant.

The invention also provides a topical mousse forming hair treatment product comprising the foamable concentrate and aerosol propellant described above, packaged in a can with hardware capable of generating a mousse on dispensing of the foamable concentrate.

Compositions according to the invention have been found to have particular benefits and advantages when the composition is one which contains an anionic styling polymer. In such circumstances, the composition according to the invention may provide not only improved foaming properties, but may also provide for good distribution of the anionic styling polymer within the hair. As such, improved styling using a composition containing an anionic styling polymer may be achieved.

In particular when the composition contains an anionic styling polymer, the composition according to the invention may be regarded as a so-called three-in-one composition, providing washing, conditioning and styling benefits.

Preferably, compositions according to the invention are also prepared such that they are free of a thickening agent. Such compositions, which typically form a foamable concentrate with a viscosity of less than 3000 centipoise (cps), have been found to have improved distribution in the hair when dispersed as a mousse composition from a propellant driven mousse container.

Preferably, compositions according to the invention comprise 85 to 98%, and more preferably 90 to 97% by weight of the aqueous foamable concentrate, with the balance being aerosol propellant.

The mousse-forming cleansing hair treatment composition or the invention comprises a foamable concentrate and an aerosol propellant. The term "concentrate" is used to refer to the liquid component of the hair treatment composition other than the propellant. The term "mousse", as used herein, is the same as foam, and refers to the dispensed product, unless otherwise specified. The composition is packaged in appropriate hardware and in an appropriate manner so as to provide a topical product which dispenses a foamed mousse, the hardware and necessary techniques for this being well known to the skilled person.

The viscosity of the foamable concentrate suitably ranges from 1 to 3000, preferably from 10 to 2000, ideally from 100 to 1000 cps.

Viscosity is measured in the conventional manner using a rotary viscometer (Brookfield Viscometer, LVT type, Rotor No.3, 12 rpm after 30 sec. at 25° C.).

In order to achieve such suitable viscosities as described above for the foamable concentrate, it is particularly preferred that the foamable concentrate be substantially free of crystalline suspending agents and polymeric thickening agents. By "substantially free" it is generally meant that the level of such agents be about 0.5% or less, preferably about 0.1% or less, ideally no more than about 0.05% by weight of the foamable concentrate. Crystalline suspending agents which are preferably excludes or present in very low levels include long chain (e.g. C8–C22) alkyl derivative materials and long chain amine oxides, such as ethylene glycol long chain esters, alkanolamides of long chain fatty acids, long chain esters of long chain Fatty acids, glyceryl long chain esters, long chain esters of long chain alkanolamides, and long chain alkyl dimethyl amine oxides. Common suspending agents of this type are ethylene glycol esters of C14–C22 fatty acids (e.g. ethylene glycol distearate), C16–C22 fatty acid alkanolamides (e.g. stearic monoethanolamide, stearic monoisopropanolamide), C16–C22 alkyl dimethyl amine oxides and N,N-dihydrocarbyl (C12–C22) amidobenzoic acid and sales thereof.

It may in some cases also be preferable, in order to achieve suitable viscosities as described above for the foamable concentrate, to incorporate a rheology modifier such as a thinner. Suitable thinners include polyethylene glycol (PEG), polypropylene glycol (PPG), sodium xylene sulphonate, sodium toluene sulphonate and urea. Preferred thinners are PEG 400 and PPG 400.

The foamable hair treatment composition comprises one or more surfactants, to provide a cleansing benefit, but is absent any substantial quantities of anionic surfactant. Surfactant may also be present as emulsifier for any emulsified particles of conditioning agent present. If anionic surfactant is present, it should be present at levels of 6 wt % or less, more preferably 4 wt % or less, even more preferably 2 wt % or less, even more preferably less than 2 wt % of the foamable concentrate. Ideally the foamable concentrate contains no anionic surfactant.

Any anionic surfactant which is present is preferably present at a ratio of less than 1:2, more preferably less than 1:5, even more preferably less than 1:10 compared to the level of other surfactants present in the concentrate. Suitable surfactants for use in compositions according to the invention are known in the art and include nonionic, cationic and zwitterionic surfactants, and mixtures thereof.

Examples of nonionic surfactants which may be used as surfactants for the hair treatment compositions are alkylphenol ethoxylates, e.g. nonylphenol ethoxylate nEO, where n is from 1 to 50, alcohol ethoxylates, e.g. lauryl alcohol nEO, where n is from 1 to 50 ester ethoxylates, e.g. polyoxyethylene monostearate where the number of oxyethylene units is from 1 to 30. A preferred species of nonionic surfactant are the n-methyl alkyl glucamides, especially those having a chain length of $C_{12}$–$C_{14}$.

Further, nonionic cleansing surfactants suitable for use in hair treatment compositions of the invention may include condensation products of aliphatic ($C_8$–$C_{18}$) primary or secondary linear or branched chain alcohols or phenols with alkylene oxides, usually ethylene oxide and generally having from 6 to 30 ethylene oxide groups. Other suitable nonionics include alkylpolyglycosides, alcohol ethoxylates and mono- or di-alkyl alkanolamides. Examples of the latter nonionics include coco mono- or di-ethanolamide and coco mono-isopropanolamide.

Amphoteric and zwitterionic cleansing surfactants suitable for use in compositions of the invention may include alkyl amine oxides, alkyl betaines, alkyl amidopropyl betaines, alkyl sulphobetaines (sultaines), alkyl glycinates, alkyl carboxyglycinates, alkyl amphopropionates, alkylamphoglycinates and alkyl amidopropyl hydroxysultaines. Examples include lauryl amine oxide, cocodimethyl sulphopropyl betaine and preferably lauryl betaine, cocamidopropyl betaine and sodium cocamphopropionate.

The total amount of surfactant present is generally from 3 to 50% by weight, preferably from 5 to 30%, more preferably from 10%0 to 25% by weight of the foamable concentrate.

In a preferred embodiment of the invention, the hair treatment composition may comprise emulsified particles of a conditioning agent.

As used herein, the term "conditioning agent" includes any material which is used to give a particular conditioning benefit to hair. For example, in shampoo compositions, materials such as moisturisers, essential oils, sun-protective or after-sun treatment materials, occlusive oils and the like may be used. Further, in shampoo compositions suitable conditioning agent materials may also include those which deliver one or more benefits relating to shine, softness, combability, wet-handling, anti-static properties, protection against damage, body, volume stylability and manageability.

Preferred conditioning agents for use in the present invention include silicones. Suitable silicones may be one or more polyalkyl siloxanes, one or more polyalkylaryl siloxanes, or mixtures thereof. The silicone is insoluble in the aqueous matrix of the composition and so is present as dispersed particles, in an emulsified form.

The viscosity of the silicone itself (i.e. not the emulsion or the final hair treatment composition) preferably ranges from 10,000 cps to 5,000,000 cps.

Suitable polyalkyl siloxanes include polydimethyl siloxanes which have the CTFA designation dimethicone, having a viscosity of up to 100,000 centistokes at 25° C. These siloxanes are available commercially from the General Electric Company as the Viscasil series and from Dow Corning as the DC 200 series. The viscosity can be measured by means of a glass capillary viscometer as set out further in Dow Corning Corporate Test Method CTM004 Jul. 20, 1970. Also suitable is polydiethyl siloxane.

Also suitable are silicone gums, such as those described in U.S. Pat. No. 4,152,416 (Spitzer), and on General Electric Silicone Rubber product Data Sheet SE 30, SE 33, SE 54 and SE 76. "Silicone gum" denotes polydiorganosiloxanes having a molecular weight of from 200,000 to 1,000,000, and specific examples include polydimethyl siloxane polymers, polydimethyl siloxane/diphenyl/methylvinylsiloxane copolymers, polydimethylsiloxane/methylvinylsiloxane copolymers and mixtures thereof.

Aminofunctional silicones which have the CTFA designation amodimethicone, are also suitable for use in the compositions of the invention, as are polydimethyl siloxanes having hydroxyl end groups (which have the CTFA designation dimethiconol).

An advantage of compositions according to the invention which contain emulsified particles is that it is thought that there are no real restrictions on the emulsified droplet size, as most droplet sizes seems to re-disperse easily.

Particle size may be measured by means of a laser light scattering technique, using a 2600D Particle Sizer from Malvern Instruments.

The amount of silicone incorporated into hair treatment compositions of the invention depends on the level of conditioning desired, and the material used. A preferred amount is from 0.01 to about 10% by weight of the foamable concentrate, although these limits are not absolute. The lower limit is determined by the minimum level to achieve desired conditioning, and the upper limit by the maximum level to avoid making the hair unacceptably greasy. We have found that an amount of silicone of from 0.5 to 1.5% by weight of the foamable concentrate, is a particularly suitable level.

A further suitable class of conditioning agents for incorporation are hair body and volume enhancing materials. Examples are cross-linked silicone gums and per-alk(en)yl hydrocarbon materials.

Suitable cross-linked silicone gums are described in WO96/31188. A preferred example is the material available from Dow Corning as DC X2-1787.

The amount of hair body and volume enhancing material incorporated into the hair treatment compositions depends on the level of enhancement desired and the material used. A preferred amount is from 0.01 to about 10% by weight of the foamable concentrate, although these limits are not absolute. The lower limit is determined by the minimum level to achieve the desired body and volume enhancing effect, and the upper limit by the maximum level to avoid making the hair unacceptably stiff. We have found that an amount of hair body and volume enhancing material of from 0.5 to 2% by weight of the foamable concentrate, is a suitable level.

According to a highly preferred embodiment, the hair treatment composition comprises an anionic polymer, which may be present in the foamable concentrate at a level of 0.001–10% by weight of the foamable concentrate. Conveniently, the anionic polymer is one which has one or more carboxylic acid groups, one or more carboxylic acid alkali metal salt groups, one or more sulphate groups, or one or more sulphonate groups, or mixtures thereof.

In a preferred embodiment of the present invention, the anionic polymer is present from about 0.001% to about 5.0%, based on the total weight of the hair treatment composition. In a more preferred embodiment of the present invention, the anionic polymer is present from about 0.2% to about 2.0%, based on the total weight of the hair care composition.

In general, the anionic polymer comprises a polymer with one or more carboxylic acid groups, one or more carboxylic acid alkali metal salt groups, one or more sulfate groups, one or more sulfonate groups and mixtures thereof. Thus, the anionic polymer may be a polymer selected from polymeric condensation products of methyl vinyl ether and maleic anhydride and salts, half acid esters and half acid amides thereof, salts of the half acid ester and/or half amide ester of the copolymeric condensation products of methyl vinyl ether and maleic anhydride, sodium salts of terpolymers of octyl acrylamide, polymeric condensation products of acrylate esters and butylaminoethyl methacrylate, acrylic acid polymers cross-linked with a polyfunctional agent, polyvinyl sulphonates, and mixtures thereof. The polyfunctional agent may preferably be an agent selected from a polyol, a polyamine, carboxymethyl cellulose and mixtures thereof.

Additionally, the anionic polymer member may contain at least one carboxylic acid group, or at least one sulfate group, or at least one sulfonate group, or a mixture thereof, and is the product of a radical polymerization reaction of an ethylenically unsaturated monomer.

The foamable concentrate in the hair treatment composition according to the invention comprises an aqueous carrier, which is generally present at a level of 20–99% by weight of the foamable concentrate.

Packaged hair treatment compositions of the invention contain an aerosol propellant. This agent is responsible for expelling the other materials from the container, and forming the mousse character.

The propellant gas can be any liquefiable gas conventionally used for aerosol containers. Examples of suitable propellants include dimethyl ether, propane, n-butane and isobutane, used singly or admixed. Other examples of suitable propellants include nitrogen, carbon dioxide and compressed air.

The amount of the propellant gases is governed by normal factors well known in the aerosol art. For mousses the level of propellant is generally from about 2 to about 15%, optimally from about 4 to about 10% for creamy foam and good sensory feel.

Compositions of this invention may contain any other ingredient normally used in hair treatment formulations. These other ingredients may include hair styling resins, colouring agents, antifoam agents, proteins, moisturising agents, antioxidants, fragrances, antimicrobials and sunscreens. Each of these ingredients will be present in an amount effective to accomplish its purpose.

Compositions of the invention are typically prepared by charging a suitable pressurisable container with the foamable concentrate, then sealing the container and charging it with propellant according to conventional techniques.

The invention will now be illustrated by the following non-limiting examples. All parts, percentages and proportions referred to are by weight unless otherwise indicated.

EXAMPLE 1

The following compositions A and C-G represent suitable topical compositions according to the invention.

| | % (active ingredient) | | | | | | |
|---|---|---|---|---|---|---|---|
| | A | B | C | D | E | F | G |
| Amphomer | — | — | — | 1.2 | — | — | 1.2 |
| Sodium Polyvinyl Sulfonate | 0.6 | 0.6 | — | — | — | — | — |
| Shellac | — | — | 0.7 | — | — | — | — |
| Gantrez S97 (PVM/MA Copolymer)* | — | — | — | — | 0.4 | 0.7 | — |
| Amodimethicone | — | — | — | — | 0.5 | — | — |
| Coceth-10 | — | — | — | — | 5.0 | — | 5.0 |
| Undeceth-9 | — | — | — | — | — | 8.0 | — |
| Cocotrimonium chloride | 1.5 | 1.5 | 1.75 | — | 1.4 | 1.9 | 2.0 |
| N-Methyl C12/14 Alkyl Glucamide | 8.0 | 8.0 | 8.0 | 12.5 | — | — | — |
| Cocoamidopropyl betaine | 4.0 | 4.0 | 4.0 | 2.0 | 8.0 | 4.0 | 8.0 |
| Coco monoethanolamide | 1.0 | 1.0 | 1.0 | 2.0 | — | 1.0 | 2.0 |
| Sodium benzoate | 0.5 | 0.5 | 0.5 | 0.5 | 0.5 | 0.5 | 0.5 |
| Phenoxyethanol | 0.4 | 0.4 | 0.4 | 0.4 | 0.4 | 0.4 | 0.4 |
| PEG 6000 Distearate | — | 2.5 | — | — | — | — | — |
| Ethanol | — | — | 1.4 | — | — | — | — |
| Fragrance | 0.5 | 0.5 | 0.5 | 0.5 | 0.5 | 0.5 | 0.5 |
| Water | to 100.0 | | | | | | |

*Neutralized with amino methyl propanol.

Formulation B was thickened with PEG 6000 disterate, and remained in the form of a flowable liquid shampoo. Formulations A and C-G were packaged in cans with mousse generating hardware, along with 7% butane propellant at a pressure of 2.7 bar. Compositions A and C-G all had initial viscosities of less than 2000 cps.

A comparative test of compositions A and B was carried out in which the compositions were assessed for lathering properties. Apart from the PEG 6000 distearate, base compositions A and B are directly comparable.

In the test, panellists assessed lather on 25 cm/12 g switches. Each panellist applied both compositions A and B to two different switches. The switches were thoroughly wetted with warm water, and 1 g of either formulation A or B was dosed into the panellists hand, and was applied to the switch to generate lather. The same process by the panellist with the other composition on the other switch.

In assessing compositions A and B, 100% of the panellists considered that lather generation was more rapid from composition A than B.

Also 50% of the panellists considered that composition A provided more lather overall, compared to 10% who considered that composition B provided more lather, and 40% who considered that compositions A and B generated the same amount of lather. The consensus was also that composition B produced lather relatively slowly, and was not easily spread through the hair, whereas composition A provided instantaneous foam, with the composition and foam being readily spread to all parts of the hair.

Compositions containing the anionic styling polymer were perceived to provide washed switches with more body, and were more easily styled than other switches washed with compositions containing no conditioning or styling components, demonstrating that compositions containing the anionic styling polymer and conditioning agents give good deposition of styling polymer and/or conditioning agents on the hair.

What is claimed is:

1. A mousse forming hair cleansing and optionally conditioning composition, comprising a foamable concentrate comprising from 10 to 25 wt. % of at least one surfactant but no more than 6 wt. % anionic surfactant, an aqueous carrier, an aerosol propellant, and no more than 0.5 wt. % of crystalline suspending agents and polymeric thickening agents, and having a viscosity of less than 3000 cps.

2. A mousse-forming hair treatment composition according to claim 1, wherein the composition additionally comprises an anionic styling polymer.

3. A mousse-forming hair treatment composition according to claim 1, wherein the foamable concentrate is free of thickening agent.

4. A mousse-forming hair treatment composition according to claim 1, wherein the composition comprises from 85 to 98 wt. % foamable concentrate and from 2 to 15 wt. % aerosol propellant.

5. A mousse-forming hair treatment composition according to claim 1, wherein the composition is totally free of anionic surfactant.

6. A mousse-forming hair treatment composition according to claim 1, wherein the composition comprises a thinner.

7. A mousse-forming hair treatment composition according to claim 1, wherein the thinner is polyethylene glycol or polypropylene glycol.

8. A mousse-forming hair treatment composition according to claim 1, which comprises nonionic surfactant.

9. A mousse-forming hair treatment composition according to claim 1, wherein the nonionic surfactant is an n-methyl alkyl glucamide surfactant having a chain length of $C_{12}-C_{14}$.

10. A mousse-forming hair treatment composition according to claim 1, wherein the anionic polymer is present in the composition at a level of from about 0.2 to about 2 wt. %.

11. A topical mousse-forming hair treatment product comprising a treatment composition according to claim 1, packaged in a can with hardware capable of generating a mousse dispensing of the foamable concentrate.

* * * * *